(12) United States Patent
Govari et al.

(10) Patent No.: US 10,173,028 B2
(45) Date of Patent: Jan. 8, 2019

(54) MAGNETIC RESONANCE IMAGING COMPATIBLE CATHETER

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Athanassios Papaioannou, Los Angeles, CA (US); Ariel Garcia, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 993 days.

(21) Appl. No.: 14/484,461

(22) Filed: Sep. 12, 2014

(65) Prior Publication Data
US 2014/0378806 A1 Dec. 25, 2014

Related U.S. Application Data

(62) Division of application No. 12/958,679, filed on Dec. 2, 2010, now Pat. No. 8,857,304.

(51) Int. Cl.
A61M 25/01 (2006.01)
A61M 25/00 (2006.01)
(Continued)

(52) U.S. Cl.
CPC ....... *A61M 25/0012* (2013.01); *A61B 5/0422* (2013.01); *A61B 5/065* (2013.01); *A61B 5/6852* (2013.01); *A61B 5/6885* (2013.01); *A61M 25/005* (2013.01); *A61M 25/0108* (2013.01); *A61M 25/0127* (2013.01);
(Continued)

(58) Field of Classification Search
CPC ..... A61B 5/0422; A61B 5/065; A61B 5/6852; A61B 5/6885; A61B 5/055; A61B 2562/12; A61B 2017/00911; A61M 25/0012; A61M 25/005; A61M 25/0108; A61M 25/0127;
(Continued)

(56) References Cited

U.S. PATENT DOCUMENTS 5,411,527 A * 5/1995 Alt ................. A61N 1/0587
600/374
5,454,795 A * 10/1995 Samson ............ A61L 29/041
600/435
(Continued)

FOREIGN PATENT DOCUMENTS

EP 0 444 728 A1 9/1991
EP 0 806 596 A1 11/1997
(Continued)

OTHER PUBLICATIONS

Extended European Search Report dated Mar. 5, 2012 from related European Application No. 11191572.4.
(Continued)

*Primary Examiner* — Lee S Cohen
*Assistant Examiner* — Erin M Cardinal
(74) *Attorney, Agent, or Firm* — Notaro, Michalos & Zaccaria P.C.

(57) ABSTRACT

A method, consisting of passing a cylindrical carbon fiber through a press so as to produce a flat ribbon. The method further includes weaving multiple strands of the flat ribbon together to create a cylindrical braid.

4 Claims, 4 Drawing Sheets

(51) Int. Cl.
| | |
|---|---|
| *D04C 1/06* | (2006.01) |
| *D04C 3/40* | (2006.01) |
| *A61B 5/06* | (2006.01) |
| *A61B 5/00* | (2006.01) |
| *A61B 5/042* | (2006.01) |
| *G01R 33/28* | (2006.01) |
| *A61B 5/055* | (2006.01) |

(52) U.S. Cl.
CPC ............... *D04C 1/06* (2013.01); *D04C 3/40* (2013.01); *G01R 33/287* (2013.01); *A61B 5/055* (2013.01); *A61B 2562/12* (2013.01); *A61M 2205/02* (2013.01); *A61M 2205/332* (2013.01); *A61M 2207/10* (2013.01)

(58) Field of Classification Search
CPC ........ A61M 2205/02; A61M 2205/332; A61M 2207/10; A61N 1/086
See application file for complete search history.

(56) References Cited

U.S. PATENT DOCUMENTS

| | | | | |
|---|---|---|---|---|
| 5,569,220 | A * | 10/1996 | Webster, Jr. ...... | A61M 25/0045 138/125 |
| 5,633,074 | A | 5/1997 | Muroi | |
| 5,701,905 | A * | 12/1997 | Esch ............ | A61B 5/0215 600/486 |
| 5,891,114 | A * | 4/1999 | Chien ............ | A61M 25/0053 138/123 |
| 5,906,606 | A | 5/1999 | Chee et al. | |
| 5,954,649 | A * | 9/1999 | Chia ............ | A61B 5/0422 600/424 |
| 6,110,591 | A | 8/2000 | Crosier | |
| 8,857,304 | B2 * | 10/2014 | Govari ............ | A61B 5/065 87/13 |
| 2003/0144718 | A1 * | 7/2003 | Zeijlemaker ......... | A61N 1/056 607/122 |
| 2003/0208252 | A1 * | 11/2003 | O'Boyle ............ | A61B 18/1492 607/122 |
| 2003/0216642 | A1 | 11/2003 | Pepin et al. | |
| 2004/0145075 | A1 | 7/2004 | Klug | |
| 2006/0095050 | A1 | 5/2006 | Hartley | |
| 2009/0282802 | A1 | 11/2009 | Cooper et al. | |
| 2009/0314765 | A1 | 12/2009 | Feng et al. | |
| 2011/0138938 | A1 * | 6/2011 | Giszter ............ | G01D 21/00 73/866.5 |
| 2011/0218603 | A1 * | 9/2011 | Victorine ............ | A61N 1/05 607/116 |

FOREIGN PATENT DOCUMENTS

| | | |
|---|---|---|
| EP | 1 374 717 A2 | 1/2004 |
| EP | 2 213 325 A1 | 8/2010 |
| JP | 04-008751 A | 1/1992 |
| JP | 06-346337 A | 12/1994 |
| JP | 6-346337 A | 12/1994 |
| JP | 2005525883 A | 9/2005 |
| JP | 2007507294 A | 3/2007 |
| JP | 2007516008 A | 6/2007 |
| JP | 2010514513 A | 5/2010 |
| WO | WO 2009/088697 A1 | 7/2009 |

OTHER PUBLICATIONS

JPO Official Action dated Feb. 16, 2016 from corresponding Japanese patent application No. 2011-263377.
Japanese office action of corresponding Japanese patent application No. 2011-263377, dated Dec. 19, 2017.

* cited by examiner

MAGNETIC RESONANCE IMAGING COMPATIBLE CATHETER

This Application is a Divisional Patent Application of U.S. patent application Ser. No. 12/958,679, now U.S. Pat. No. 8,857,304, filed Dec. 2, 2010.

FIELD OF THE INVENTION

The present invention relates generally to invasive probes, and specifically to producing a magnetic resonance imaging compatible catheter.

BACKGROUND

A wide range of medical procedures involve placing objects, such as sensors, tubes, catheters, dispensing devices, and implants, within the body. When placing a medical probe fitted with position sensors within the body, a reference image of the body cavity being treated is typically presented on a display. The reference image assists a medical professional in positioning the probe to the appropriate location(s).

SUMMARY OF THE INVENTION

An embodiment of the present invention provides a method, including,
passing a cylindrical carbon fiber through a press so as to produce a flat ribbon; and
weaving multiple strands of the flat ribbon together to create a cylindrical braid.

Typically, the press includes a roller press. In one embodiment the carbon fiber has a diameter no greater than 500 µm.

In a disclosed embodiment the method includes repeating passing the cylindrical carbon fiber through the press one or more times until the flat ribbon meets defined dimensional specifications. Typically, the dimensional specifications define a rectangle having a width no greater than 500 µm, and a thickness no greater than 500 µm.

In an alternative embodiment the cylindrical braid is flexible. Typically, the method includes cutting the flexible cylindrical braid to a pre-defined cut length, thereby creating a section; covering the section with a flexible biocompatible sheath; and positioning one or more functional elements within the cut length of the braid, thereby producing a magnetic resonance imaging compatible medical probe.

Each of the one or more functional elements may be selected from a list consisting of an electrode, a position sensor, a force sensor, cabling and tubing. The magnetic resonance imaging compatible probe typically consists of only non-magnetic materials.

There is further provided, according to an embodiment of the present invention, a medical probe, which has proximal and distal ends and includes:
a flexible cylindrical braid woven from multiple strands of a flat carbon ribbon;
a flexible biocompatible sheath that is formed over the braid; and
one or more functional elements running within the braid between the proximal and the distal end of the probe.

Typically, the probe includes only non-magnetic materials.

Each of the one or more functional elements may be selected from a list consisting of an electrode, a position sensor, a force sensor, cabling and tubing. Typically, the flat carbon ribbon has dimensional specifications defining a rectangle having a width no greater than 500 µm, and a thickness no greater than 500 µm.

There is further provided, according to an embodiment of the present invention, a method, including:
weaving a flexible cylindrical braid from multiple strands of a flat carbon ribbon;
forming a flexible biocompatible sheath over the braid so as to produce a probe having proximal and distal ends; and
running one or more functional elements within the braid between the proximal and the distal ends of the probe.

There is further provided, according to an embodiment of the present invention, a method, including:
forming a flexible biocompatible sheath over a flexible cylindrical braid woven from multiple strands of a flat carbon ribbon, so as to produce a probe having proximal and distal ends; and
running one or more functional elements within the braid between the proximal and the distal ends of the probe.

BRIEF DESCRIPTION OF THE DRAWINGS

The disclosure is herein described, by way of example only, with reference to the accompanying drawings, wherein.

DETAILED DESCRIPTION OF EMBODIMENTS

During some medical procedures, magnetic resonance imaging (MRI) is used to assist in visualizing detailed internal structures of the body. To produce an image using MRI, a radio frequency transmitter in an MRI system transmits an electromagnetic field. In response to the electromagnetic field, cells in the body transmit electromagnetic signals, which are detected by a scanner. The MRI image is then produced based on the received electromagnetic signals.

Since MRI uses strong magnetic fields, any magnetic material in the area being visualized may distort the MRI image. In some instances, exposing a magnetic object within the body to the MRI's strong magnetic field may cause a trauma to the patient due to movement of the magnetic object exposed to the magnetic field.

Medical probes, such as catheters, commonly contain a braided steel reinforcing layer for mechanical strength. This sort of steel layer, however, may create problematic effects when exposed to the strong magnetic field from the MRI system as described supra.

Embodiments of the present invention provide a method and apparatus for producing a carbon ribbon, which when braided, can be used to produce a medical probe with a cylindrical carbon braid as reinforcement. In some embodiments, a cylindrical carbon fiber is conveyed through a press such as a roller press, producing a flat, thin carbon ribbon. The ribbon is then woven into a cylindrical braid, which can be used as a reinforcement layer for a carbon-braided probe.

Carbon-braided probes produced using embodiments of the present invention are typically comparable in both strength and flexibility to steel-braided probes, and are unaffected by the MRI's magnetic field. Furthermore, a carbon-braided probe can be used in other applications, in addition to procedures using MRI. For example, in multi-catheter procedures, the non-magnetic carbon braid in the catheter may be helpful in reducing magnetic field disturbance, which can otherwise affect position and force measurements made by other catheters.

System Description

Figure 1A:
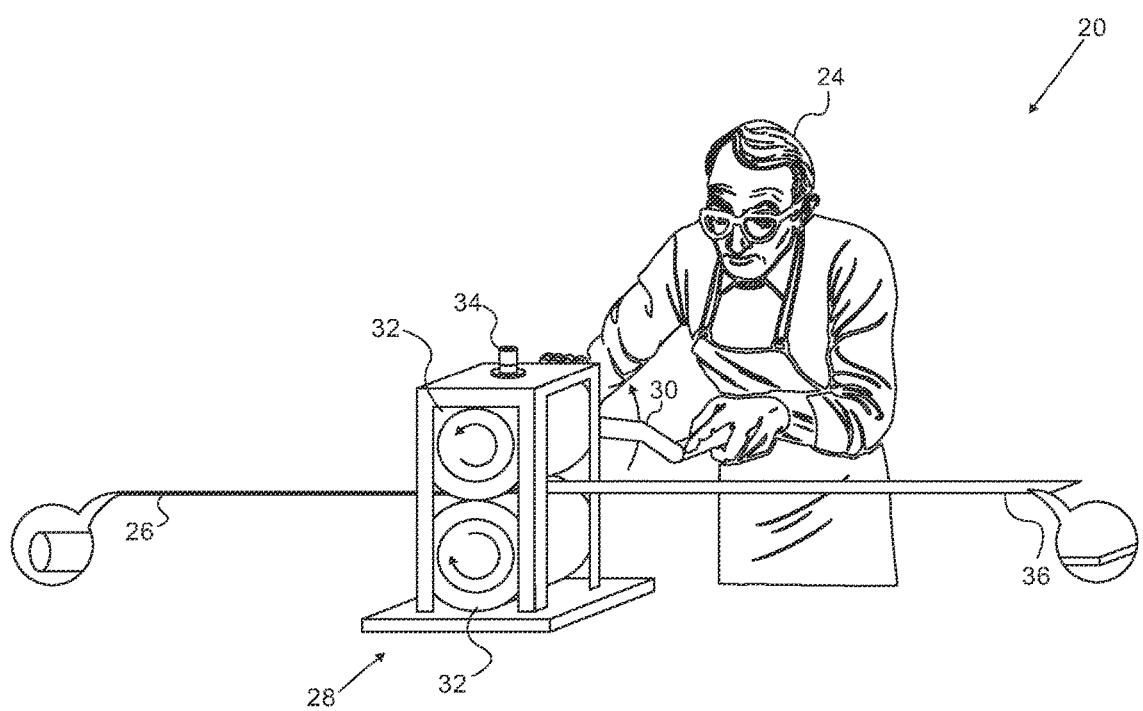
FIG. 1A is a pictorial illustration of an apparatus for producing a carbon ribbon, in accordance with an embodiment of the present invention.

FIG. 1A is a pictorial illustration of an apparatus 20 for producing a carbon ribbon 36, in accordance with an embodiment of the present invention. An operator 24 inserts a cylindrical carbon fiber 26 into a roller press 28, and rotates a handle 30 to advance the carbon fiber through the roller press. In some embodiments, carbon fiber 26 may have a diameter between approximately 50 μm and approximately 500 μm.

Roller press 28 comprises two rollers 32, handle 30 and a pressure dial 34. Rotating pressure dial 34 increases or decreases the distance between the two rollers. Handle 30 is coupled to one or both of rollers 32. Operator 24 rotating handle 30 (counter-clockwise, in the example shown in FIG. 1A) conveys the carbon fiber between the two rollers, thereby producing flat, thin carbon ribbon 36. Alternatively, roller press 28 may include a motor coupled to one or both of rollers 32 in order to convey carbon fiber 26 between the two rollers. Using the carbon ribbon whose dimensions are described supra, the dimensional specifications of ribbon 38 produced by roller press 28 has a width between 50 μm and 500 μm, and a thickness between 50 μm and 500 μm. In some embodiments, operator 24 may insert multiple carbon fibers 26 simultaneously into roller press 28 thereby producing multiple flat carbon ribbons 36.

Figure 1B:
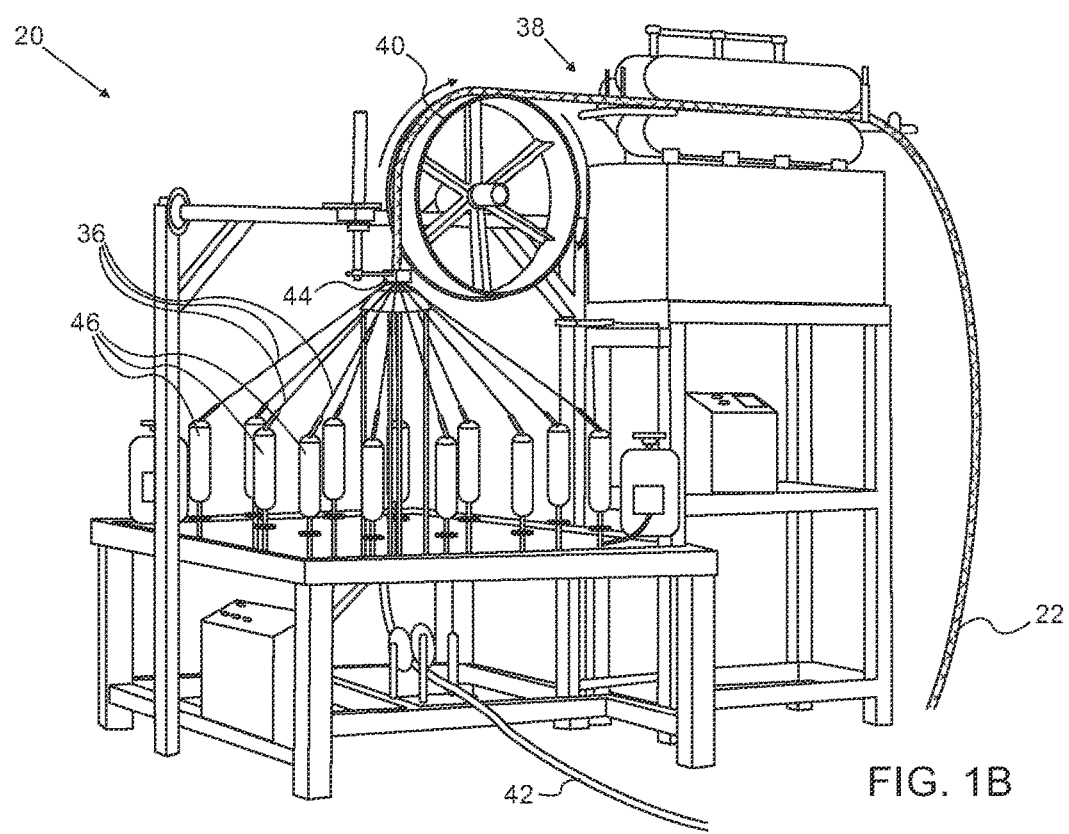
FIG. 1B is a pictorial illustration of a braiding apparatus used for producing a braid of the carbon ribbon, in accordance with an embodiment of the present invention.
Figure 1C:
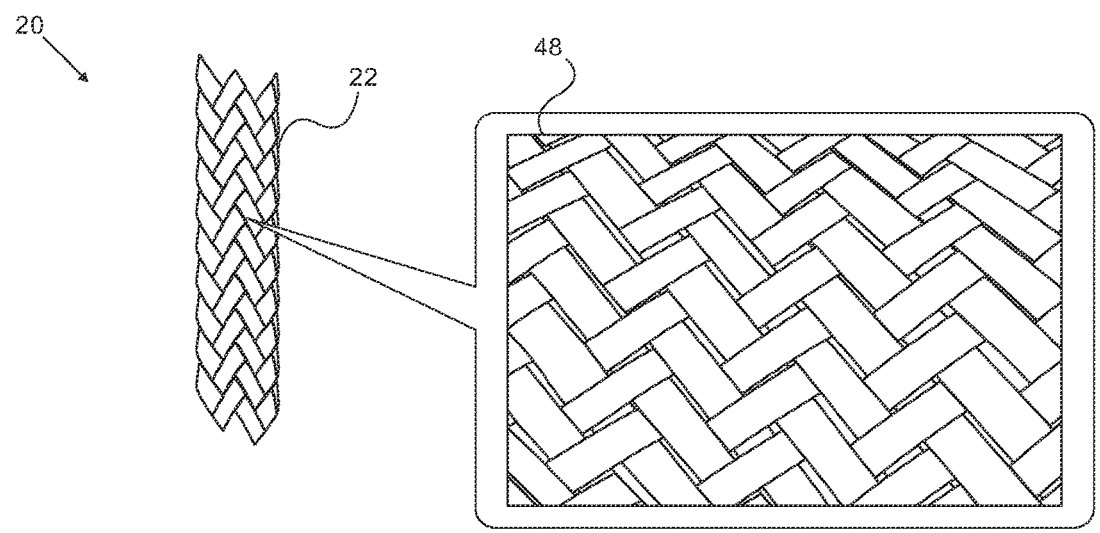
FIG. 1C is a magnified pictorial illustration of the braid produced by the braiding apparatus, in accordance with an embodiment of the present invention.

FIG. 1B is a pictorial illustration of a braiding apparatus 38, and FIG. 1C is a magnified pictorial illustration of a braid 48 produced by the braiding apparatus, in accordance with embodiments of the present invention. Braiding apparatus 38 is configured to create a cylindrical carbon braid 22 from ribbon 36. As a rotating wheel 40 conveys a flexible plastic tubing 42 through the braiding machine, a braiding mechanism 44 conveys multiple ribbons 36 from multiple spools 46, and weaves braid 48 (FIG. 1C) surrounding the plastic tubing, thereby producing cylindrical carbon braid 22.

Producing an MRI-Compatible Catheter

Figure 2:
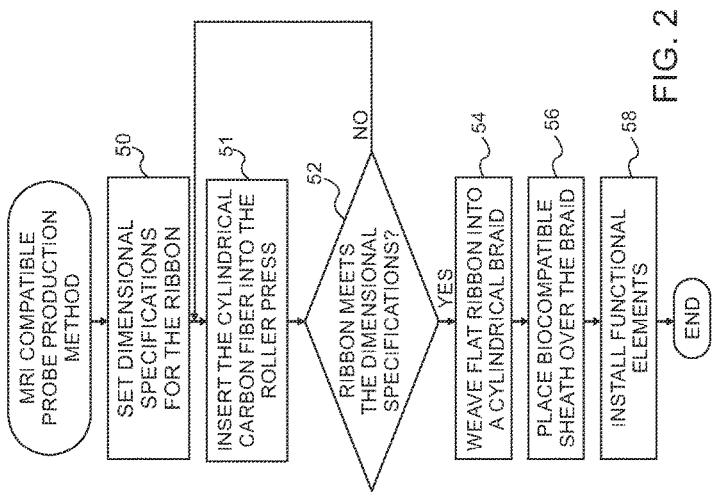
FIG. 2 is a flow diagram that schematically illustrates a method of producing a magnetic resonance imaging (MRI) compatible probe, in accordance with an embodiment of the present invention.

FIG. 2 is a flow diagram that schematically illustrates a method of producing a magnetic resonance imaging (MRI) compatible probe in accordance with an embodiment of the present invention. In an initial step 50, operator 24 defines a range of dimensional specifications (i.e., length and width) for carbon ribbon 36. The ranges are typically based on the specifications of carbon ribbon 36, which may include ribbons of different dimensions. It will be appreciated that one of ordinary skill in the art may determine suitable dimensional ranges for the ribbon without undue experimentation.

In a compression step 51, operator 24 inserts cylindrical carbon fiber 26 into roller press 28, where rollers 32 compress the carbon fiber, thereby creating carbon ribbon 36. In a comparison step 52, if ribbon 36 does not meet the dimensional specifications defined in step 50 (i.e., width and thickness), then the method returns to step 51. Typically, several passes through press 28 may be required to meet the defined dimensional specifications.

If, however, ribbon 36 meets the defined dimensional specifications, then in a weaving step 54, operator 24 loads the ribbon to spools 46 of braiding apparatus 38, which then weaves the ribbon into cylindrical carbon braid 22. In a first probe producing step 56, operator 24 cuts braid 22 to a pre-defined cut length to create a section of the braid and covers the section with a flexible, insulating, biocompatible material (also referred to herein as a sheath). Finally, in a second probe producing step 58, operator 24 positions functional elements, such as cabling and/or tubing, within the braid, thereby producing an MRI-compatible probe, where the functional elements typically run between proximal and distal ends of the probe.

Figure 3:
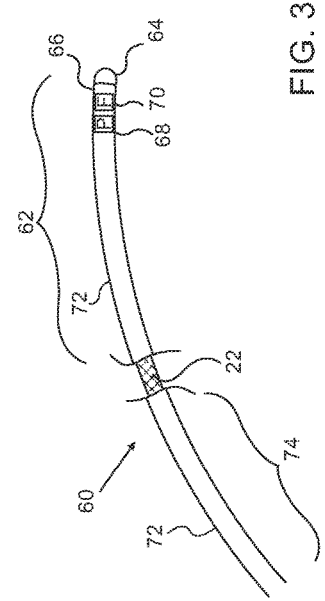
FIG. 3 is a schematic detail view showing a distal end of the MRI-compatible probe, in accordance with an embodiment of the present invention.

FIG. 3 is a schematic side view of an MRI-compatible probe 60, in accordance with an embodiment of the present invention. Specifically, FIG. 3 shows functional elements of probe 60 used in creating a map of cardiac electrical activity. An electrode 64 at a distal tip 66 of the probe senses electrical signals in cardiac tissue. Alternatively, multiple electrodes (not shown) along the length of the probe may be used for this purpose. Electrode 64 is typically made of a metallic material, such as a platinum/iridium alloy or another suitable material.

A position sensor 68 generates a signal that is indicative of the location coordinates of distal tip 66. Position sensor may comprise an electrode, wherein impedances between the electrode and additional electrodes positioned outside a patient's body are measured to determine the position of the electrode. In alternative embodiments, position sensor 68 may comprise a tri-coil position sensor (for example, as is implemented in the CARTO™ system produced by Biosense Webster, Inc., Diamond Bar, Calif.) or an ultrasonic position sensor. Although FIG. 3 shows a probe with a single position sensor, embodiments of the present invention may utilize probes with more than one position sensors.

A force sensor 70 senses contact between distal tip 66 and endocardial tissue, by generating a signal that is indicative of the pressure exerted by distal tip 66 on the tissue.

Probe 60 is covered by a biocompatible, flexible sheath 72. Sheath 72 is shown cut away in FIG. 3 in order to expose cylindrical carbon braid 22, which is covered by the sheath. In embodiments of the present invention, functional elements (e.g., electrode 64, position sensor 68, force sensor 70, and any cabling) are within sheath 72 and run between a distal end 62 and a proximal end 74 of the probe. The functional elements are typically constructed using non-magnetic materials. Using non-magnetic materials such as the platinum/iridium alloy described supra enables probe 60 to be MRI-compatible.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A magnetic resonance imaging-compatible catheter, which has proximal and distal ends and comprises:
   a flexible cylindrical braid woven from multiple strands of a flat carbon ribbon, wherein the braid consists of the strands of flat carbon ribbon, one or more force sensors and one or more ultrasonic position sensors;
   a flexible biocompatible sheath that is formed over the braid; and
   wherein the one or more force sensors and the one or more ultrasonic position sensors are woven within the braid between the proximal and the distal end of the catheter.

2. The magnetic resonance imaging-compatible catheter according to claim 1, wherein the catheter consists of only nonmagnetic materials.

3. The magnetic resonance imaging-compatible catheter according to claim 1, wherein the flat carbon ribbon has dimensional specifications defining a rectangle having a width no greater than 500 μm, and a thickness no greater than 500 μm.

4. A magnetic resonance imagine-compatible catheter, which has proximal and distal ends and comprises:
   a flexible cylindrical braid woven from multiple strands of a flat carbon ribbon wherein the braid consists of the strands of flat carbon ribbon, one or more force sensors made of a platinum/iridium alloy and one or more ultrasonic position sensors made of a platinum/iridium alloy;
   a flexible biocompatible sheath that is formed over the braid; and
   wherein the one or more force sensors and the one or more ultrasonic position sensors are woven within the braid between the proximal and the distal end of the catheter,
   wherein, and
   wherein the catheter consists of only nonmagnetic materials.

* * * * *